US008069418B2

(12) United States Patent
Monteleone (10) Patent No.: US 8,069,418 B2
(45) Date of Patent: Nov. 29, 2011

(54) MEDICAL INFORMATION SYSTEM AND USER INTERFACE SUPPORTING TREATMENT ADMINISTRATION

(75) Inventor: Rand J. Monteleone, Acton, MA (US)

(73) Assignee: Draeger Medical Systems, Inc, Andover, MA (US)

( * ) Notice: Subject to any disclaimer, the term of this patent is extended or adjusted under 35 U.S.C. 154(b) by 1994 days.

(21) Appl. No.: 10/410,820

(22) Filed: Apr. 10, 2003

(65) Prior Publication Data

US 2004/0021693 A1 Feb. 5, 2004

Related U.S. Application Data

(60) Provisional application No. 60/399,866, filed on Jul. 31, 2002, provisional application No. 60/400,296, filed on Aug. 1, 2002.

(51) Int. Cl.
*G06F 3/048* (2006.01)
(52) U.S. Cl. .................. 715/781; 715/764; 715/780
(58) Field of Classification Search .............. 345/781; 715/781, 764, 780
See application file for complete search history.

(56) References Cited

U.S. PATENT DOCUMENTS

| | | | | |
|---|---|---|---|---|
| 4,878,175 A | * | 10/1989 | Norden-Paul et al. | 705/2 |
| 5,842,175 A | * | 11/1998 | Andros et al. | 705/3 |
| 5,942,986 A | | 8/1999 | Shabot et al. | 340/825.44 |
| 5,950,168 A | | 9/1999 | Simborg et al. | 705/3 |
| 5,960,403 A | * | 9/1999 | Brown | 705/2 |
| 6,401,072 B1 | | 6/2002 | Haudenschild et al. | 705/3 |
| 6,983,423 B2 | * | 1/2006 | Dvorak et al. | 715/781 |
| 7,782,507 B2 | * | 8/2010 | Matsumoto | 358/527 |
| 2002/0010679 A1 | | 1/2002 | Felsher | 705/51 |
| 2002/0082865 A1 | * | 6/2002 | Bianco et al. | 705/2 |
| 2002/0083075 A1 | | 6/2002 | Brummel et al. | 707/102 |
| 2002/0087088 A1 | | 7/2002 | Brodnick | 600/509 |
| 2002/0194029 A1 | * | 12/2002 | Guan et al. | 705/3 |
| 2003/0036683 A1 | * | 2/2003 | Kehr et al. | 600/300 |
| 2003/0050801 A1 | | 3/2003 | Ries et al. | 705/2 |

FOREIGN PATENT DOCUMENTS

| | | |
|---|---|---|
| WO | WO 94/13198 | 6/1994 |
| WO | WO 98/59487 | 6/1998 |
| WO | WO 01/88825 A2 | 5/2001 |

* cited by examiner

*Primary Examiner* — Weilun Lo
*Assistant Examiner* — Shashi Becker
(74) *Attorney, Agent, or Firm* — Jack Schwartz & Associates, PLLC (57) ABSTRACT

A system advantageously populates Flowsheet data fields with predetermined exemplary patient parameter data in response to user selection of a designated displayed trigger parameter and enables user preview of Flowsheet format including the exemplary data resulting from tentative configuration settings without exiting a configuration window. A user interface display system supports entry of medical information concerning administration of treatment to a patient. A display generator generates at least one display image for use in configuring a display image to be used in supporting entry of information concerning administration of medication to a patient. The at least one display image includes data entry elements supporting user selection of a plurality of predetermined data item values associated with an individual parameter and a display window including particular user entered predetermined data item values in a format substantially the same as the format the particular predetermined data item values are to have in a configured display image.

22 Claims, 11 Drawing Sheets

MEDICAL INFORMATION SYSTEM AND USER INTERFACE SUPPORTING TREATMENT ADMINISTRATION

This is a non-provisional application of provisional application Ser. No. 60/399,866 by R. J. Monteleone filed Jul. 31, 2002 and of provisional application Ser. No. 60/400,296 by R. J. Monteleone filed Aug. 1, 2002.

FIELD OF THE INVENTION

This invention is related to processing and displaying medical information in a network environment for use in supporting administration of treatment to a patient.

BACKGROUND OF THE INVENTION

Patient medical parameter data is acquired, collated, stored and displayed for use in providing patient clinical care in hospitals, clinics, and other healthcare delivery settings. Patient medical parameter data may include vital signs ventilator information, infusion pump data associated with fluid delivery and other data. Such patient medical parameter data is typically displayed on a patient monitoring device screen in a trend indicative chart with a time axis. This type of chart is commonly termed a Flowsheet. A patient monitoring device is usually located at a patient bedside or nursing station in a hospital ward or in an intensive care, surgical or other location and may be connected to a network such as the Internet, a LAN, a WAN or an intra-net for acquiring patient parameter data from local sources (e.g., patient attached sensors) or remote sources (e.g., a remotely stored electronic patient record). The Flowsheet is an electronic chronological chart of patient parameter information that substitutes for a paper vital sign Flowsheet.

It is desirable that an electronic Flowsheet offer similar or better features and flexibility than a paper Flowsheet chart that it replaces. Such paper Flowsheet charts are used by healthcare personnel to record patient Fluid Intake and Output information and other parameters in many different ways. Known electronic Flowsheet systems are limited in the features they offer. Such feature limitations include limited user capability to specify default or exemplary values for patient parameters and the manner of exemplary value presentation. Such exemplary parameter values may identify medication amount, medication units of measure, fluid type, fluid volume, dose units of measure, and drip rate for each medication of a medication drip parameter, for example. Known systems typically constrain a user to configure a Flowsheet to include exemplary parameter values for a limited, fixed set of parameters, and a limited, fixed set of data items (data fields) associated with the parameters components or fields within those parameters. Such limitations on the use of exemplary values compromise Flowsheet usability since the presentation of exemplary values in a Flowsheet reduces Flowsheet configuration time and reduces error by providing guidance for data entry.

Known systems are further limited in Flowsheet data format preview capability. The complexity of Flowsheet configuration means that it is difficult for a user to envision the look of a Flowsheet resulting from selected configuration options. Known systems typically require a user to exit a configuration popup menu (saving the configuration setting upon exit) and enter data for a test patient, for example, in order to view a resultant Flowsheet presentation and verify that the configuration conformed to requirements. This is a clumsy and burdensome procedure involving saving a configuration setting in a configuration menu, navigating to a test Flowsheet and entering test data for display and review in this test Flowsheet. Further, if amendment is necessary, a user needs to navigate back to an appropriate configuration popup menu and make alterations and repeat the review procedure. These restrictions mean that known systems provide electronic Fluids Flowsheet that fail to replicate the look, features and flexibility of Flowsheet paper charts. A system according to invention principles addresses these limitations and derivative problems.

SUMMARY OF THE INVENTION

A system initiates population of Flowsheet data fields with a comprehensive set of predetermined exemplary patient parameter data and associated data items in response to user selection of a designated particular trigger parameter or data item. The system enables a user to initiate preview display of a Flowsheet resulting from configuration data entered via a configuration menu in response to a user configuration menu command. A user interface display system supports entry of medical information concerning administration of treatment to a patient. The system includes a display generator for generating at least one display image enabling user selection of a plurality of data items associated with an individual patient parameter, and a particular data item of the plurality of data items as a trigger data item. A command processor receives commands entered via a medical information display image and searches storage to retrieve predetermined data item values to populate corresponding data item fields in the medical information display image in response to user selection of an image element, associated with the trigger data item, and displayed in the medical information display image. The at least one display image includes a window for displaying data item values in a format substantially the same as the format the data item values are to have in a configured display image.

DETAILED DESCRIPTION

The inventors have advantageously recognized that it is desirable to provide an electronic Flowsheet that is flexibly configurable to include exemplary values for any or all patient parameters and associated data items including any data item that is created by a user and associated with a parameter. A user interface system enables a user to designate any patient parameter or data item associated with a patient parameter as a trigger item. The system initiates population of Flowsheet data fields with a predetermined set of exemplary (e.g., default) patient parameter data and associated data items in response to user selection of a designated displayed trigger parameter or data item. As an example, a user configures a Flowsheet with an exemplary value for one or more of the multiple data items identifying corresponding different additive medications comprising an intra-venous (IV) fluid. A user further designates a data item identifying a particular additive medication in the Flowsheet as a trigger item. Thereby, in response to user selection of the displayed trigger additive medication data item, the Flowsheet is populated with an exemplary value comprising an amount and unit of measure for one or more of the additive medications. The system similarly enables a user to establish a Flowsheet informational data field and any patient parameter or associated data item as a trigger for initiating population of the informational data field in response to user selection of a trigger data item displayed in the Flowsheet. Thereby, a Flowsheet is configurable to display a warning message when a particular additive medication data item is selected, for example.

The system enables a user to initiate preview display of a Flowsheet resulting from configuration data entered via a configuration menu in response to user command via the configuration menu. Specifically, the system supports Flowsheet configuration by providing a window for displaying particular user entered exemplary patient parameter data item values (such as Fluids intake and output parameters) in a format substantially the same as the format the values are to have in a configured Flowsheet display image. The system advantageously enables a user to preview Flowsheet look and feel resulting from entered tentative configuration settings and to avoid the necessity of having to exit a configuration window and save the tentative settings. A user is thereby able to efficiently modify settings and arrive at a desired Flowsheet configuration without unnecessary burdensome configuration update and navigation steps.

Figure 1:
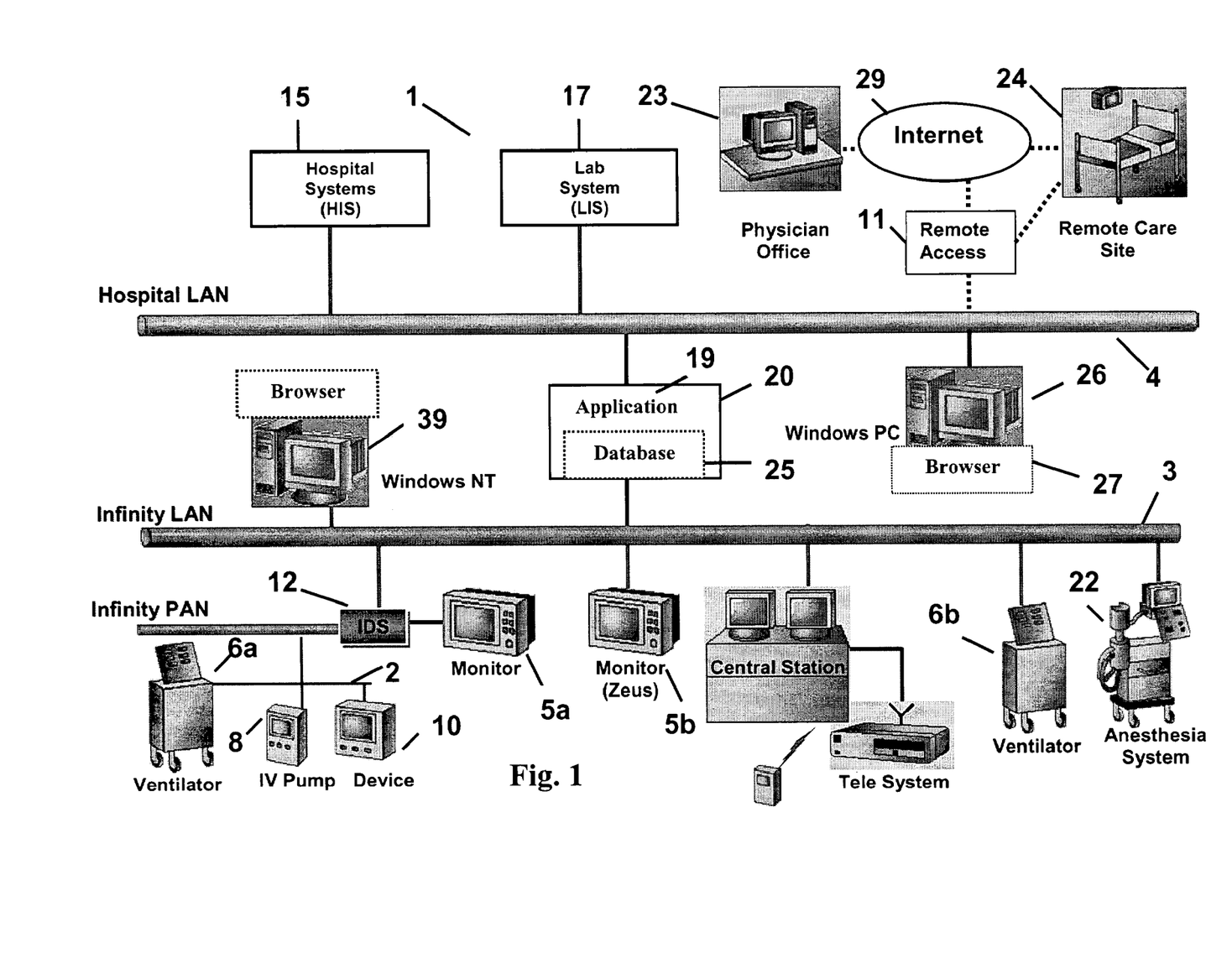
FIG. 1 is a block diagram of a communication network with various devices, according to the principles of the invention.

FIG. 1 is an exemplary block diagram of a communication network incorporating server 20 hosting executable application 19 providing a trend indicative user interface display of patient parameters (termed a Flowsheet) within identified acquisition time intervals. A Flowsheet may display different types of parameters associated with, for example, Intra-Venous fluids, drip administered medications, blood products, blood pressure, ventilation, vital signs, blood oxygen concentration, and infusion pump fluid delivery. Particular parameters contain different pieces of data that are important to describe a particular fluid. Further, hospitals typically employ different practices concerning the data to be included with each parameter and the manner of displaying this data. A system advantageously populates. Flowsheet data fields with predetermined exemplary patient parameter data in response to user selection of a designated displayed trigger parameter and enables user preview of Flowsheet format including the exemplary data resulting from tentative configuration settings without exiting a configuration window.

In an alternative embodiment, the executable application providing the Flowsheet user interface may be resident in another processing device in any part of the network shown in FIG. 1. Communication network 1 (FIG. 1) is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown in FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a care unit such as a patient's room within a nursing station to administer care to a particular patient and to monitor the particular patient. Various medical devices may be connected via MIB 2; examples shown in FIG. 1 comprise a ventilator 6a, IV (Intravenous) Pump 8 or other medical equipment 10. MIB 2 is typically connected to a second level LAN network 3 through an Interface Docking Station (IDS) device 12, for interfacing to Ethernet-compatible LAN network 3. The LAN 3 may be for example, an Infinity LAN, marketed by Siemens Medical System. This higher-level LAN 3 is typically, though not necessarily, used by other care units such as a particular department within a hospital, such as an intensive care unit or surgery unit, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a ventilator 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 11 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 11 may also be part of server 20, to be described below, instead of standing alone, as well know in the art.

According to the principles of the present invention, executable application 19 (or multiple applications in another embodiment) resides on central server on LAN 3 for gathering and processing data from the peripheral medical devices or facilities coupled to LAN 3 or hospital LAN 4, including laboratory results supplied via laboratory system 17 connected through an HL7 interface, for example. Additional medical parameter data including additional laboratory results acquired from any number of medical devices such as those shown in FIG. 1 may be obtained by server 20 using ASTM messaging, for example. The acquired medical parameters associated with a given patient, including laboratory test results, are acquired from the medical devices on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. An example of server 20, is a Prometheus server, marketed by Siemens Medical System. The server may be hosted, for example, by a computer system that is capable of running Microsoft NT operating system.

Application 19 provides a user interface trend indicative display of patient parameters (a Flowsheet) covering a time period comprising user selectable acquisition time intervals. A user selectable acquisition time interval represented by a column in the Flowsheet covers a time period (typically 3 minutes to 4 hours or another user selectable range) in which patient parameters are acquired. Application 19 automatically filters acquired patient parameter data by selecting a patient parameter value for display in a Flowsheet column representing an individual acquisition time interval. Specifically, the selected patient parameter value is incorporated in an Internet compatible (web based) Flowsheet column representing the individual acquisition time interval. Application 19 advantageously enables a user to customize the Flowsheet trend indicative display of an individual patient parameter.

Figure 2:
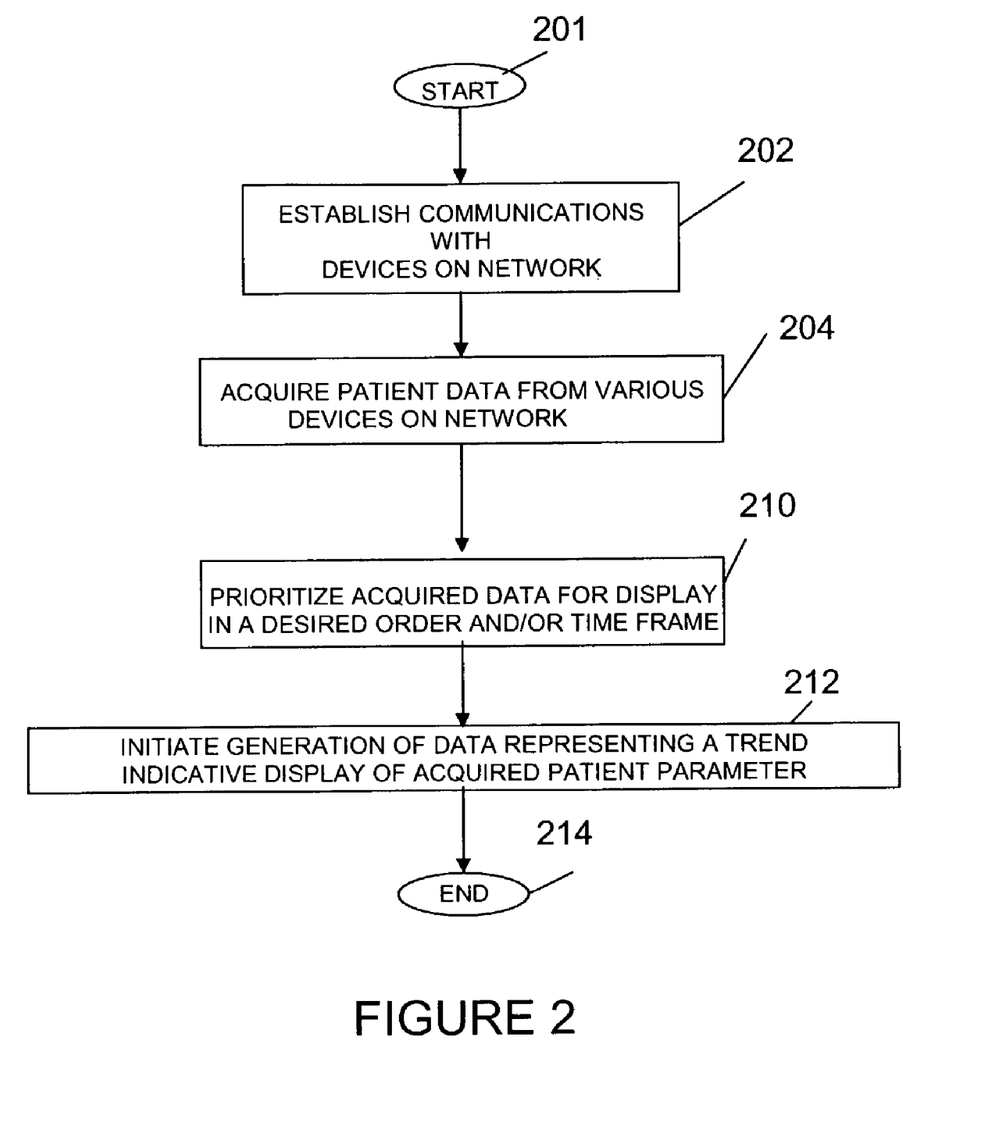
FIG. 2 represents a flowchart of a method for providing a user interface, according to the present invention.

FIG. 2 shows in flow chart form, functions that are performed by executable application 19. Application 19 establishes communication with devices on the network as shown in step 202 after the start at step 201. This is done, for example, by using IP protocol and the known IP device address for each device on the network 1 (FIG. 1), in conjunction with any higher application-layer protocols, as known in the art. Once communication is established between server 20 and the other devices, application 19, in step 204, starts to acquire parameters that are being monitored, laboratory results and settings selected for the various devices. As previously mentioned, laboratory results may be obtained through an HL7 interface with LIS 17, or via ASTM or MIB point of care (POC) medical devices depicted in FIG. 1. Types of acquired monitored patient parameters include, blood pressure parameters, respiratory or ventilation parameters, vital sign parameters, blood oxygen concentration representative parameters, infusion pump parameters associated with fluid delivery, drip medication related parameters and other fluid related parameters, for example.

Medical data and laboratory results may be continuously, periodically or non-periodically acquired and correlated with a given patient for storage in relational data base 25 within server 20. Data base 25 may be of the type used for storing relational data such as the Microsoft SQL server. In addition, application 19 may obtain patient parameter data and patient data comprising medical laboratory results that are first entered and stored, for example, in laboratory system 17 of FIG. 1. Also, application 19 may acquire healthcare provider entered medical notes for display. At step 210, application 19, in response to a user command, prioritizes and stores acquired patient data in server 20, in a desired order and/or time frame for display. Application 19 in step 212 generates data representing a Flowsheet trend indicative display of prioritized acquired patient parameters.

In one aspect of the present invention, a user may use a Microsoft Windows compatible PC 26 or Windows NT compatible PC 39 as shown in FIG. 1, or any other processing devices capable of running a menu generating program such as a web browser program (e.g., Microsoft Internet Explorer or Netscape Navigator, etc.) to view a Flowsheet, medical parameters and laboratory results information associated with a given patient. That is, a user may use a web browser on any processing device, as long as a communication connection can be made to server 20 and application 19, to make requests and view information acquired and stored in data base 25. This is advantageous, since a doctor may for example, gain access to a Flowsheet or laboratory test results from, for example, a remote physician's office 23, without having to access a dedicated terminal. Of course, a user can simply use a keyboard and/or a mouse or any other user interface devices to enter a user selection or request on a user computer, as is known in the art. Application 19 is therefore capable of collating and formatting medical data to be compatible with, for example, HTML (HyperText Mark-up Language) programming language for displaying data on a web browser. Application 19 is also responsive to, for example, HTTP (HyperText Transfer Protocol) commands originated from a user's web browser for making a request. The process of FIG. 2 ends at step 214.

Figure 3:
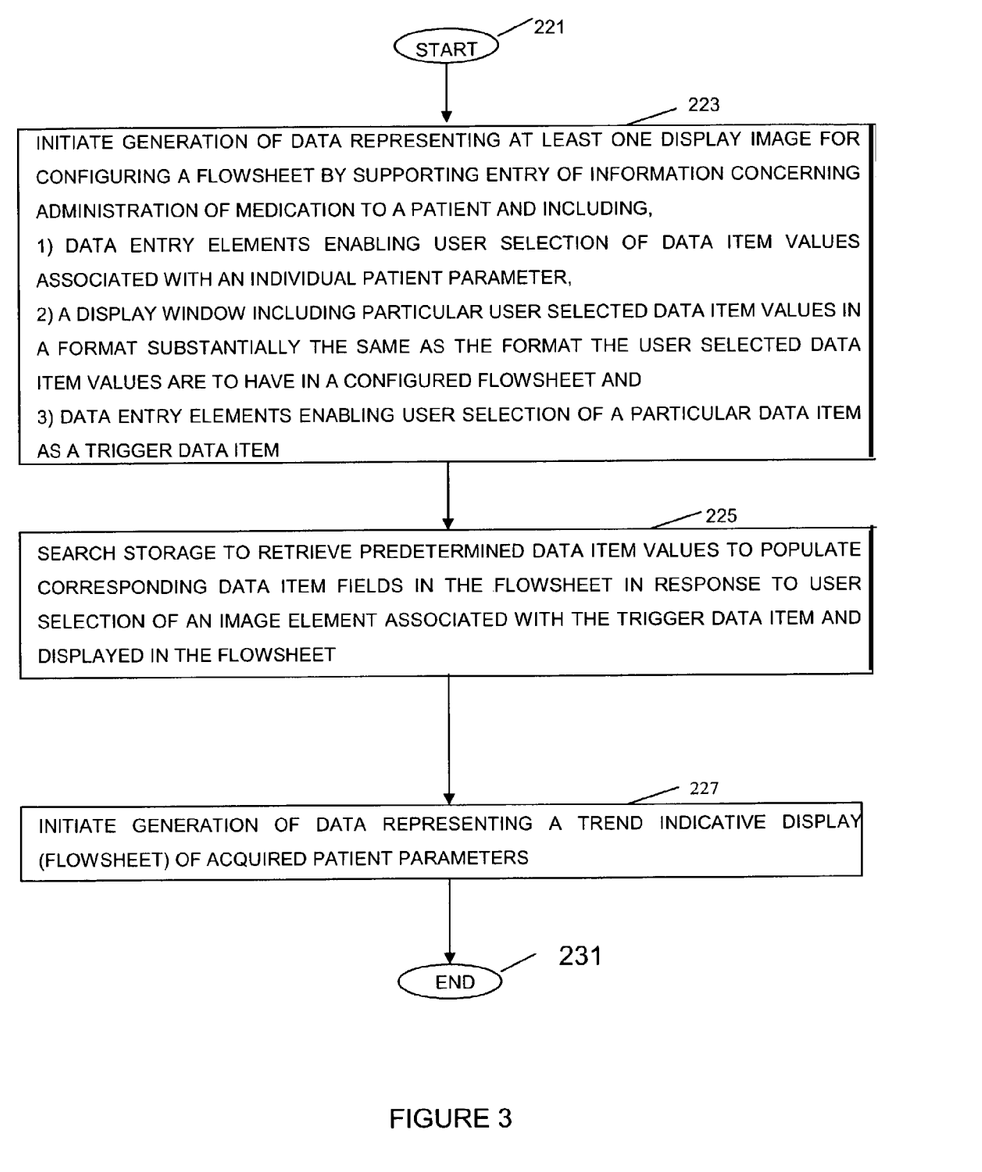
FIG. 3 represents a flowchart of a method for configuring and previewing Flowsheet exemplary patient parameter data, according to the present invention.

FIG. 3 represents a flowchart of a method for configuring and previewing Flowsheet exemplary patient parameter data. In step 223, following the start at step 221, application 19 initiates generation of display images for use in configuring a display image to be used in supporting entry of information concerning administration of medication to a patient. The display images include data entry elements supporting user selection of a plurality of predetermined data item values associated with an individual parameter. The display images also support user configuration of a Flowsheet for presenting selected data items. Data items associated with a patient parameter that may be displayed in a Flowsheet include, a volume of patient fluid infusion or output, a rate of volume of patient fluid infusion or output, a blood bank identification number, a blood type identifier, a dosage indicator, an indicator of a drip medication, an intra-venous fluid type identifier, a site on a patient associated with the patient parameter or a healthcare worker identifier, for example. Display images support user selection of patient intake, output, and medication parameters used in a fluids administration Flowsheet, for example.

Figure 4:
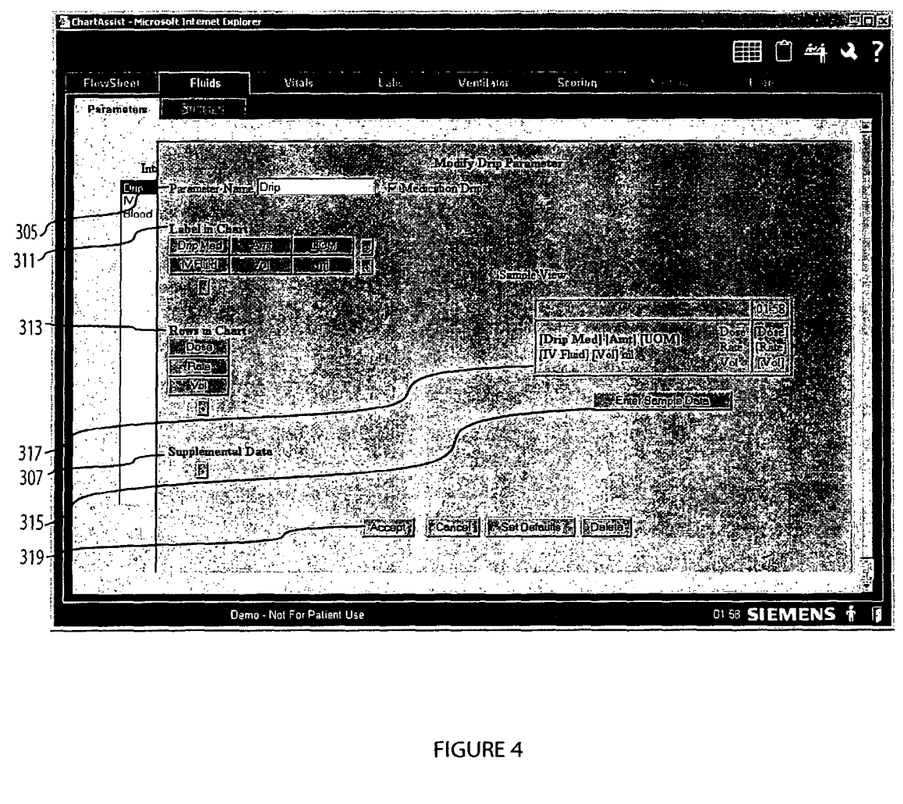
FIGS. 4-9 show user interface display images supporting a user in configuring a user interface system to automatically select and adapt a Flowsheet for trend indicative display of patient parameters in response to patient relocation to a different care unit, according to the present invention.

The display images also include a display window including particular user entered predetermined exemplary data item values in a format substantially the same as the format the particular predetermined exemplary data item values are to have in a configured display image. FIG. 4 shows a user interface image enabling user selection and configuration of parameter data including associated labels, data items, and supplemental data for presentation in a trend indicative display (a Flowsheet). Specifically, the FIG. 4 image enables user selection of labels, data items, and supplemental data associated with a Drip patient parameter identified by entry of the parameter name via item 305. The FIG. 4 user interface display image enables a user to initiate selection of a parameter label (via activation of an item in area 311), one or more data items associated with a patient parameter (via activation of item 313) and supplemental data associated with a patient parameter (via activation of item 307). The supplemental data is omitted from the Flowsheet main display but is viewable in a popup menu together with Flowsheet data items for a particular parameter in response to user selection of a parameter label in a Flowsheet display image, for example. In response to a user selecting entered data items to be associated with a parameter in a Flowsheet display image (via an accept button of bar 319), a user is presented with a preview display of the parameter and data items in table 317 as illustrated in FIG. 4. Preview table 317 displays data items in a format substantially the same as the format the data items are to have in a configured display. Brackets encompassing data item names (or labels) in table 317 identify the location where user entered exemplary data values of corresponding data items are to be inserted.

Figure 5:
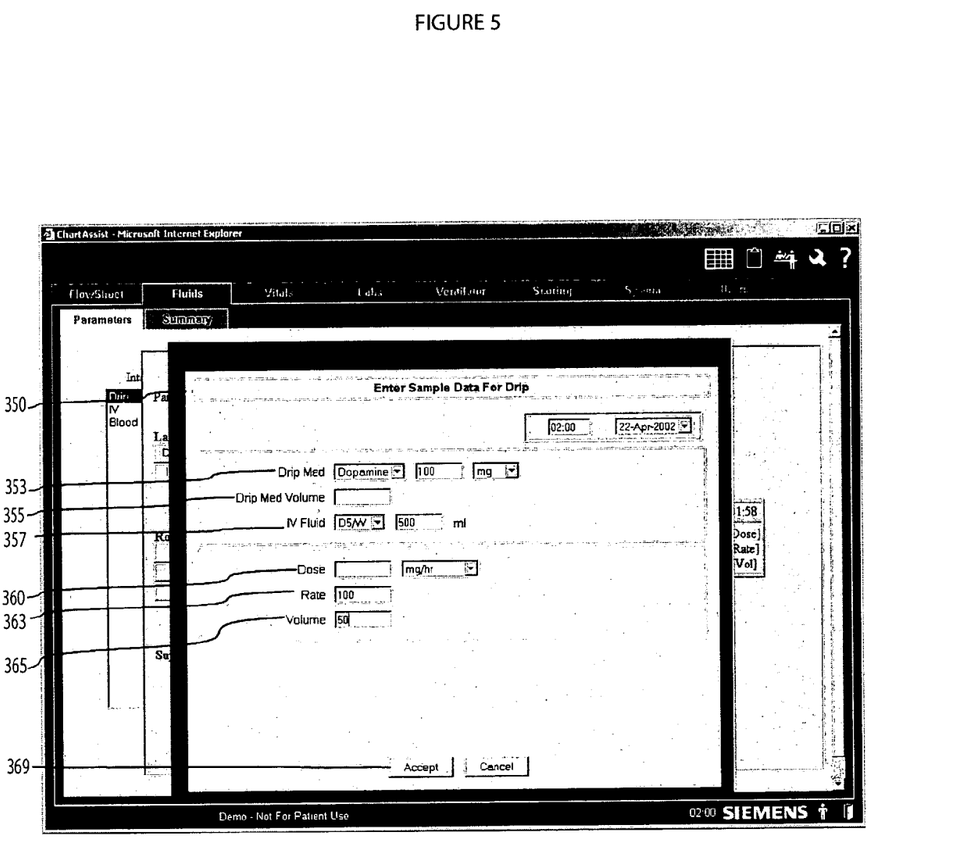

In response to user activation of Enter Sample Data button 315 of FIG. 4 popup menu popup 350 of FIG. 5 is generated.

Figure 6:
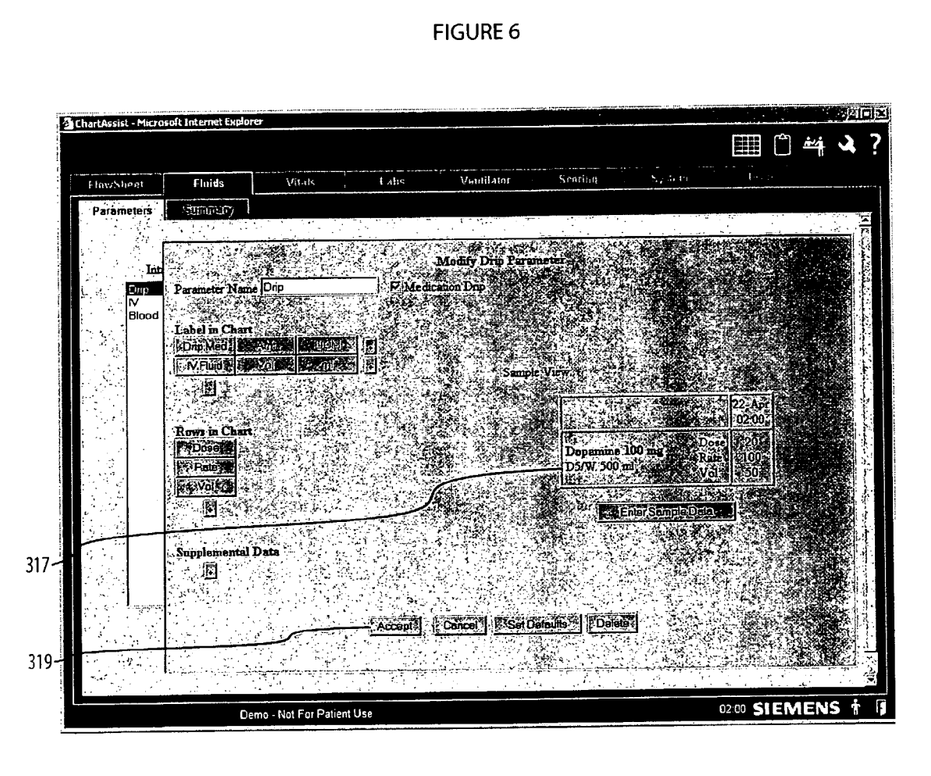

A similar popup menu is employed by a user to enter real data for a patient. A user employs popup menu 350 to enter data for the data items selected in the menu of FIG. 4. Specifically, a user selects data for Drip Med item 353, Drip Med Volume 355, IV Fluid 357, Dose 360, Rate 363 and Volume 365 and enters the selected data by selecting an accept button of bar 369. In response to user selection of an accept button in popup menu 350 of FIG. 5, The data entered via menu 350 is entered into the preview table 317 of FIG. 4 as shown in FIG. 6. Preview table 317 displays the entered data item information in a format substantially the same as the format the data item information is to have in a configured display. Consequently, preview table 317 of FIG. 6 shows data items occupying one or more character lines and as they appear in the leftmost column of a Flowsheet as illustrated in box 330 of the Flowsheet of FIG. 9. A user saves the entered data for use as illustrated in preview table 317 of FIG. 6 by activation of an accept button in bar 319 or modifies the data item information using the menu of FIG. 5 without saving the data item information in a database. This advantageously enables parameter data items to be configured for presenting in a Flowsheet using exemplary data and without a user having to leave configuration menus. In contrast, in known systems, a user employs configuration menus to enter candidate Flowsheet parameter data item information, leaves the configuration menus to view the candidate format in a real Flowsheet format and re-enters the configuration menu for amendment of the candidate format. This is a slow, burdensome process.

Figure 7:
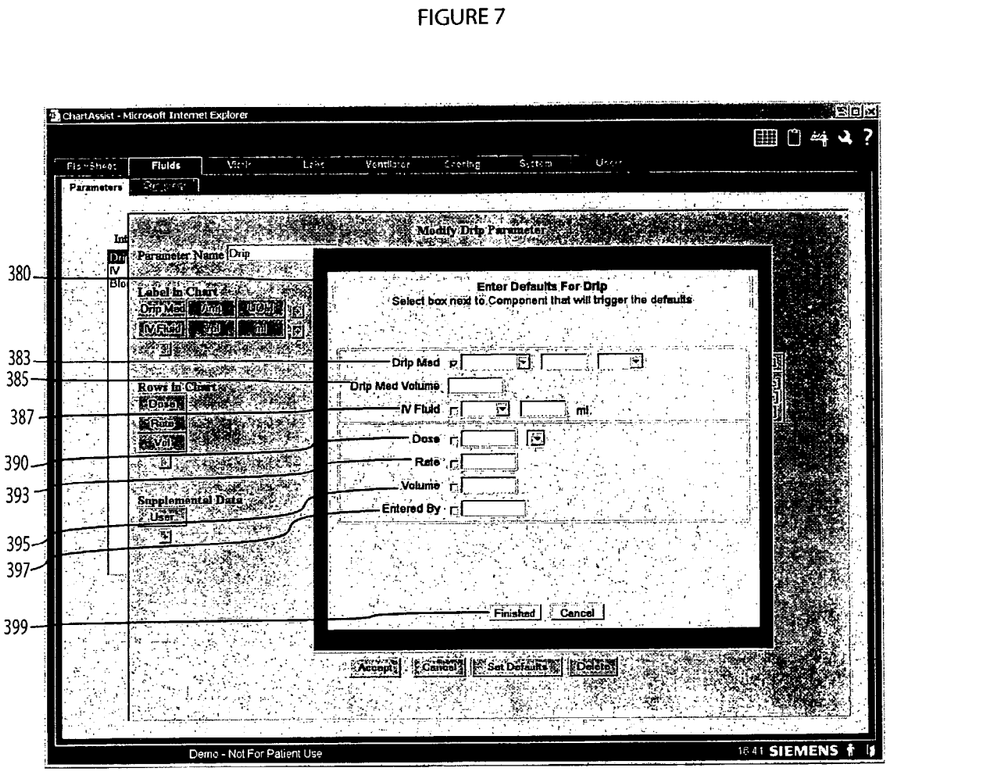

The display images generated in step 223 (FIG. 3) also include a display window enabling a user to select a particular data item of the created data items as a trigger data item. In response to user selection of a trigger data item in a Flowsheet image, application 19 in step 225 (FIG. 3) searches storage to retrieve predetermined data item values to populate corresponding data item fields in the Flowsheet. Upon user selection of Set Defaults button of bar 319 (FIG. 4 or 6), popup menu 380 of FIG. 7 is displayed. Menu 380 enables a user to set exemplary values for fluid or medication parameter data items 383-397. The exemplary values may include normal, typical, test, default or sample values, for example and to select a particular data item as a trigger data item. Thereby a user is advantageously able to select exemplary values for any parameter and any data item associated with any parameter and to select any data item associated with a parameter as a trigger for initiating display of exemplary values. A user selects one data item associated with a parameter as a trigger data item by selecting a small check box adjacent to data item labels of items 383 and 387-399 in menu 380. Menu 380 illustrates user selection of Drip Med item 383 as a trigger data item, for example. One data item associated with a parameter is selectable as a trigger data item in the preferred embodiment but in other embodiments multiple data items of a parameter may be selected as trigger data items.

Figure 8:
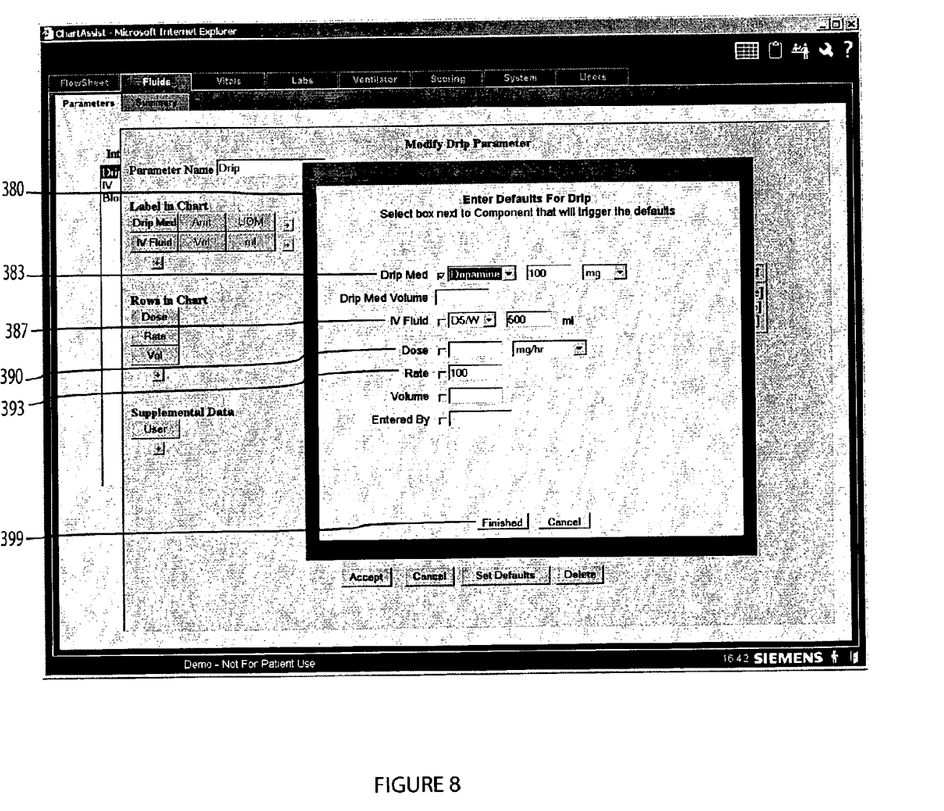

FIG. 8 shows menu 380 with data entered for Drip Med item 383 (the trigger item), IV Fluid item 387, Dose item 390 and Rate item 393. The entered values are displayed in response to user selection of the Drip Med trigger item 383 in a displayed Flowsheet image. No exemplary value is displayed for a data item left blank in menu 380. The user entered exemplary values are stored in a list in temporary storage in response to user selection of a different value for trigger data item 383 (or in response to user selection of a Finished button in bar 399).

Figure 9:
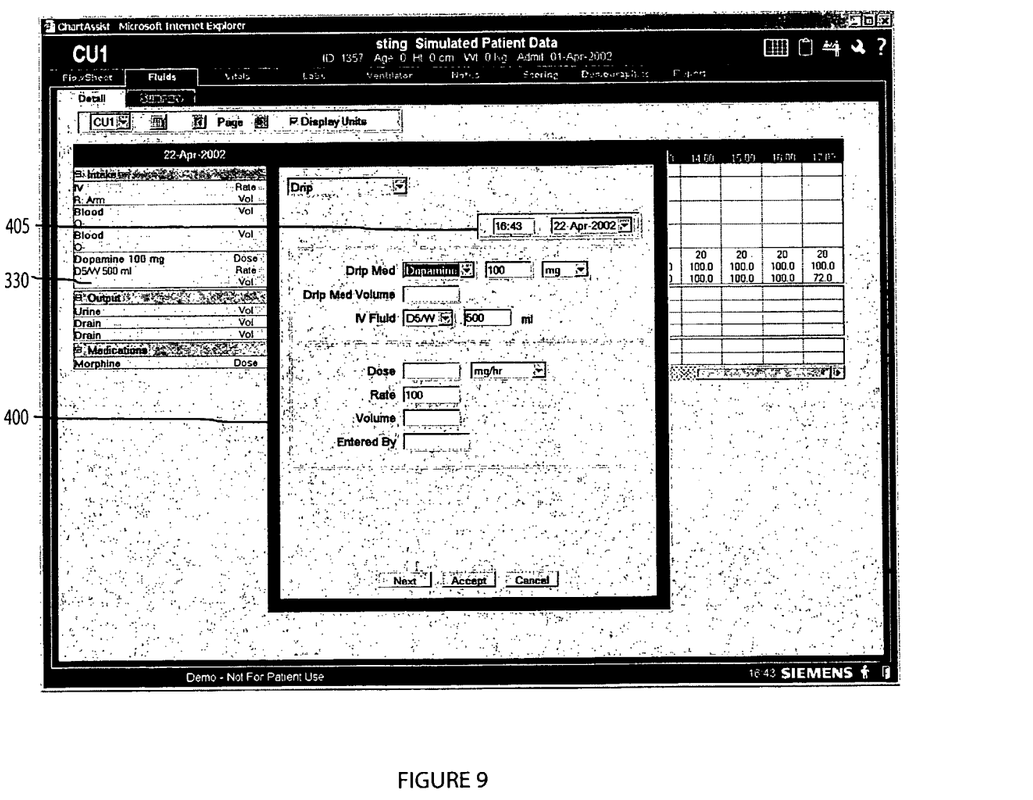

Upon selection of the exemplary values for the data items associated with a parameter, a user activates a finish button of bar 399. As a result, the parameter and data item values currently held in temporary storage are stored as Flowsheet configuration values in database 25 (FIG. 1) indicating completion of parameter and data item configuration. A user is able to modify exemplary values at any time using menu 380. Further, in response to user selection of a value for a trigger data item in menu 380 (e.g., for data item 383), application 19 checks to see whether any exemplary values have previously been entered for this trigger data item. Application 19 examines the temporary storage, configuration memory and database 25 for a previously entered trigger data item value. If an exemplary trigger data item value is detected, menu 380 is populated with exemplary values corresponding to the parameter data items associated with this trigger data item value. These values are subsequently modifiable by a use within menu 380. A system advantageously populates Flowsheet data fields with predetermined exemplary patient parameter data in response to user selection of a designated displayed trigger parameter and enables user preview of Flowsheet format including the exemplary data resulting from tentative configuration settings without exiting a configuration window. Further, FIG. 9 illustrates popup menu 400 employed by a user to enter parameter and data item values for a particular patient. In response to user selection of a new value for a trigger data item in menu 400, application 19 queries database 25 to determine if any exemplary values have been previously entered for data items associated with the trigger data item and populates popup menu 400 with these exemplary values. Menu 400 further identifies a time and date of storage of the populated exemplary value in box 405. Box 330 of the leftmost column of the Flowsheet of FIG. 9 also shows data items occupying multiple character lines in the format in which they are advantageously displayed in preview table 317 of FIG. 6. Application 19 further receives commands entered via a configuration display image to identify user entered exemplary data item values in storage for deletion.

Figure 10:
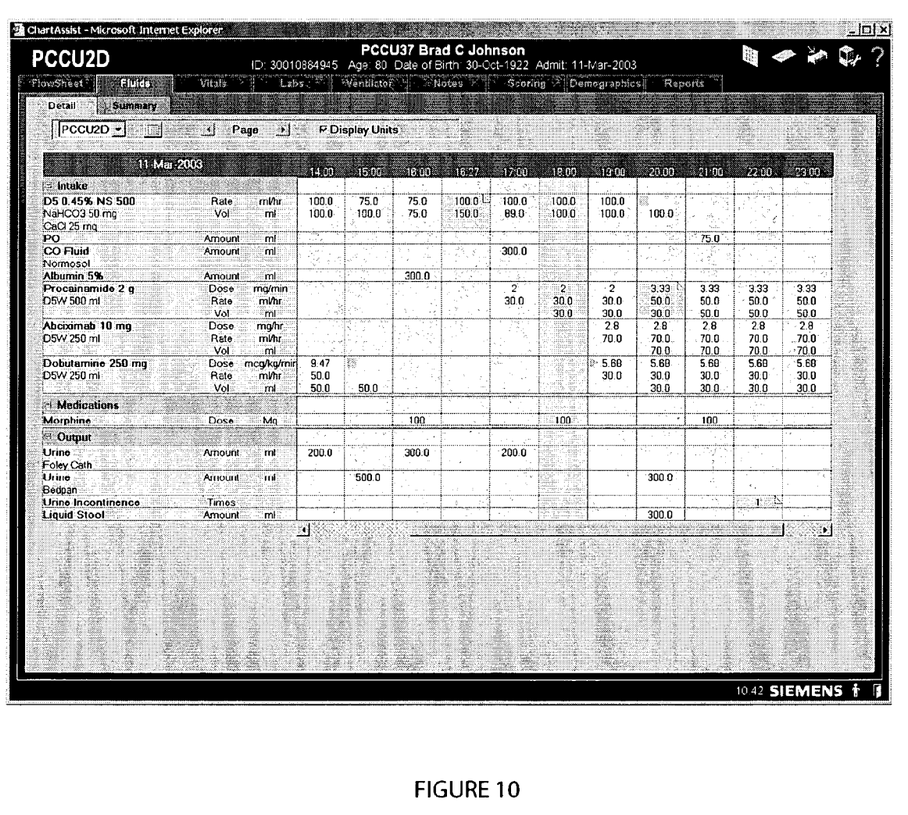
FIG. 10 show a configured Flowsheet trend indicative display of acquired patient parameters, according to the present invention.

Returning to the flowchart of FIG. 3, application 19 in step 227, initiates generation of image data representing a configured Flowsheet trend indicative display of previously acquired patient parameters as illustrated in FIG. 10. The Flowsheet format of FIG. 10 shows patient parameter data in tabular display format. The process of FIG. 3 ends at step 231.

Figure 11:
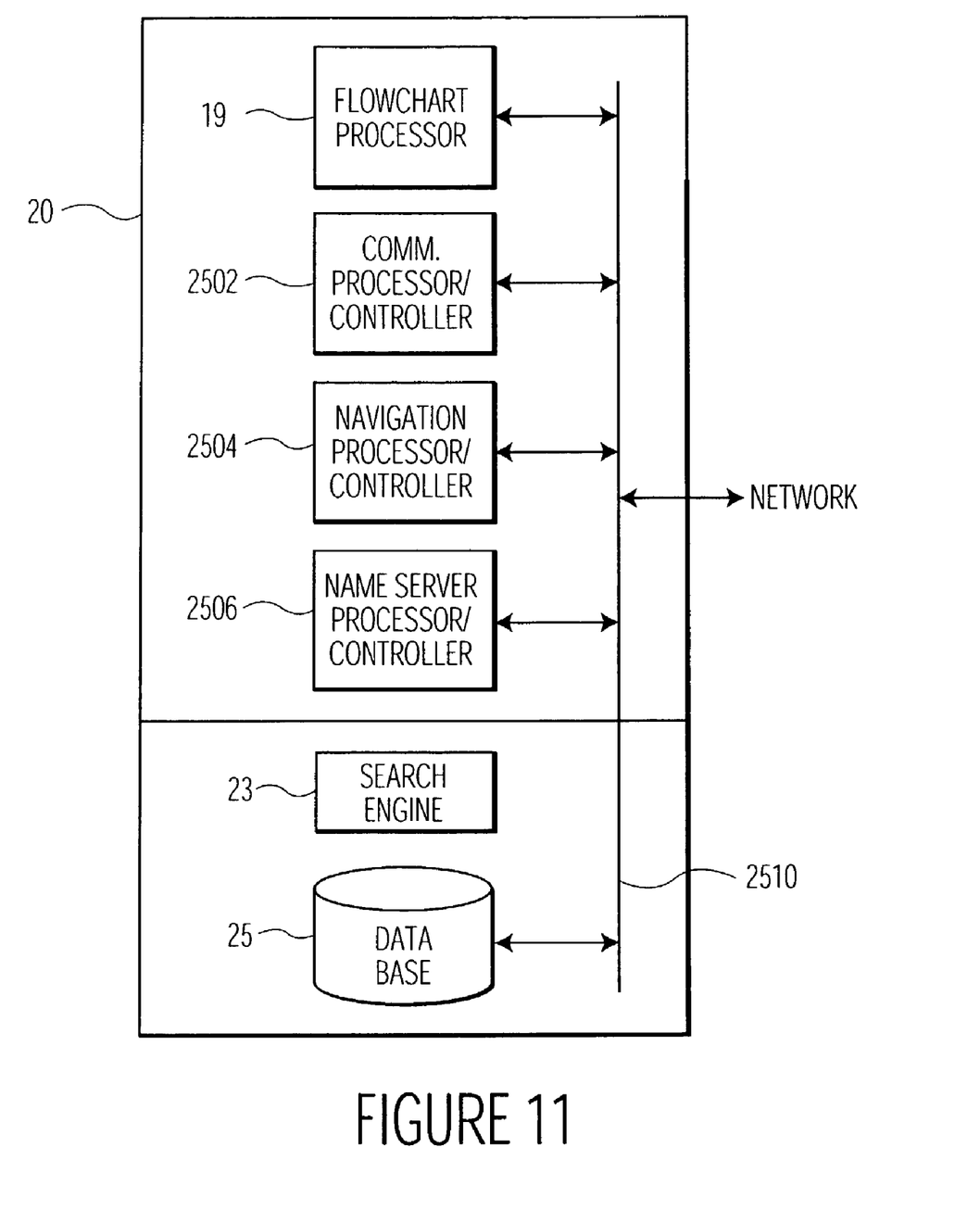
FIG. 11 is a block diagram of a server having functionality in accordance with the present invention.

FIG. 11 shows a block diagram of an exemplary embodiment of server 20 (FIG. 1) including functions in accordance with the present invention for generating data for configuring and presenting a Flowsheet trend indicative display and for managing, collating, searching and updating data base 25 containing patient medical information. Executable applications or processors operative to carry out instructions for performing the various functions described herein include an executable application 19 for performing Flowchart related processing and communications processing module 2502 that acquires the patient data including the monitored parameters allocated to a given patient from the network and collates the information for storage in data base 25. Navigation collation processor 2504 operates in conjunction with the web browser and display generator software to collate and prioritize parameters for display to the user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The Flowchart user interface display images, systems and processes presented in FIGS. 1-11 are not exclusive. Other Flowchart configuration and presentation display images, systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. The Flowchart user interface functions supporting flexible, user friendly, Flowchart configuration and may be used in any application involving preview and conditional population of presentation formats.

What is claimed is:

1. A user interface display system supporting entry of medical information concerning administration of treatment to a patient, comprising a processor including:
   a display generator for generating a display image that enables a user to configure a visual format of a medical information display image by selecting a location of a plurality of predetermined data item values in a medical information display image to be used in supporting entry of information concerning administration of medication to a patient and including,
   (a) data entry elements supporting user selection of said plurality of predetermined data item values associated with an individual patient parameter,
   (b) a user-selected particular data item of said plurality of data items for use as a trigger data item for initiating population of at least one of a data field and an informational data field with an exemplary set of at least one of data field values and informational values associated the with selected trigger data item previously stored in a storage medium, and
   (c) a preview display window that displays a preview of the medical display image in the user-configured layout and includes said populated data fields in the user-configured a visual format substantially the same as the visual format said populated data fields are to have in said medical information display image, the preview window enabling a user to selectively view a modification of at least one of said selected plurality of predetermined data item values associated with an individual patient parameter and said trigger data item of the user-configured visual format without exiting the preview display window within the display image.

2. A system according to claim 1, including
a command processor for initiating generation of data representing said display window including particular user entered predetermined data item values in response to user command.

3. A system according to claim 1, including
a command processor for receiving a command entered via a set up display image to at least one of, (i) save user entered predetermined data item values in storage, (ii) identify user entered predetermined data item values in storage for deletion and (iii) incorporate selected predetermined data item values in said display window in said display format substantially the same as the format said particular predetermined data item values are to have in a configured display image.

4. A system according to claim 1, wherein
one or more of said display images enables user selection of predetermined values for any data item associated with any of a plurality of parameters associated with administered treatments.

5. A system according to claim 1, wherein
said predetermined data item values comprise at least one of, (a) normal values, (b) typical values, (c) exemplary values, (d) test values, (e) sample values and (f) default values.

6. A system according to claim 1, wherein
said preview display window includes said particular user entered predetermined data item values in a table format substantially the same as a format said particular predetermined data item values are to have in medical information display image.

7. A system according to claim 1, wherein
said display window includes data item indicative labels for replacement by particular user entered predetermined data item values in response to user selection of said predetermined data item values.

8. A user interface system according to claim 1, wherein
said individual parameter includes at least one of, (a) a blood pressure parameter, (b) a ventilation parameter, (c) a vital sign parameter, (d) a blood oxygen concentration representative parameter, (e) an infusion pump parameter associated with fluid delivery, (f) a drip medication related parameter and (g) another fluid related parameter.

9. A user interface system according to claim 1, wherein
a data item associated with a patient parameter comprises at least one of, (a) volume data to be used in patient fluid infusion or output calculation, (b) a rate for use in calculation of volume of patient fluid infusion or output, (c) a dose, (d) a unit of measure, (e) a quantity and (f) a medication identifier.

10. A user interface display system for displaying medical information concerning administration of treatment to a patient, comprising:
   a display generator that generates a display image that enables a user to configure a visual format of a medical information display image by generating tentative configuration information, said display image enables user selection of,
   (a) a plurality of data items associated with an individual patient parameter, and
   (b) a particular data item of said plurality of data items as a trigger data item, and
   a command processor for searching storage to retrieve predetermined data item values to populate corresponding data item fields in said medical information display image with an exemplary set of at least one data item value associated with the selected trigger item in response to user selection of an image element, said image element being associated with said trigger data item and displayed in said medical information display image; and
   a preview display window within the generated display image that displays a preview of the medical display image using said tentative configuration information to display the user-configured layout, said preview of the medical display image includes said populated data item fields in a layout associated with the user-configured visual format substantially the same as the visual format said populated data items fields are to have in said medical information display image, the preview window enabling a user to modify the selected data items associated with an individual patient parameter and the selected trigger data item.

11. A system according to claim 10, wherein any of said plurality of data items associated with said individual parameter is selectable as said particular data item acting as said trigger data item.

12. A system according to claim 10, wherein said at least one display image enables user selection of exemplary values for any data item associated with any of a plurality of parameters associated with administered treatments.

13. A system according to claim 12, wherein said exemplary data item values comprise at least one of, (a) typical values, (b) test values, (c) sample values and (d) default values.

14. A system according to claim 10 wherein a predetermined data item value comprises at least one of, (a) a value of a patient parameter and (b) a value of a data item associated with a patient parameter, (c) information concerning a patient parameter, (d) information concerning a data item associated with a patient parameter and (e) a data item label.

15. A system according to claim 14, wherein said information concerning said patient parameter and said information concerning a data item associated with said patient parameter comprises at least one of, (a) a warning message concerning a particular medication and (b) administration data concerning a particular medication.

16. A system according to claim 10, wherein said command processor initiates generation of data representing a display window including user entered predetermined data item values in a format substantially the same as the format said predetermined data item values are to have in a configured display image.

17. A user interface display system for processing medical information concerning administration of treatment to a patient, comprising:
a display generator for generating a display image that enables a user to configure a visual format of a medical information display image by user selection of,
(a) a plurality of data items associated with an individual patient parameter for display in a preview display window in a user-configured visual format substantially the same as the visual format said data items are to have in a medical information display image, the preview window enabling a user to selectively view a modification of said selected data items associated with the individual patient parameter without exiting the preview display window within the display image, and
(b) a particular data item of said plurality of data items as a trigger data item; and
a command processor that searches a memory to retrieve an exemplary set of data values associated with the selected trigger data item to populate data item fields in said medical information display image in response to user selection of an image element associated with said trigger data item, said image element being displayed in said medical information display image.

18. A user interface system according to claim 17, wherein said individual parameter includes at least one of, (a) a blood pressure parameter, (b) a ventilation parameter, (c) a vital sign parameter, (d) a blood oxygen concentration representative parameter, (e) an infusion pump parameter associated with fluid delivery, (f) a drip medication related parameter and (g) another fluid related parameter.

19. A user interface system according to claim 17, wherein said medical information display image comprises a Flowsheet.

20. A user interface system according to claim 17, wherein a data item comprises at least one of, (a) volume data to be used in patient fluid infusion or output calculation, (b) a rate for use in calculation of volume of patient fluid infusion or output, (c) a dose, (d) a unit of measure, (e) a quantity and (f) a medication identifier.

21. A method for displaying medical information concerning administration of treatment to a patient, comprising the steps of generating, by a processor:
generating a display image enabling a user to configure a visual format of a medical information display image by user selection of,
(a) a plurality of data items associated with an individual patient parameter, and
(b) a particular data item of said plurality of data items as a trigger data item, and
searching by a command processor storage to retrieve an exemplary set of predetermined data item values associated with the selected trigger data item to populate corresponding data item fields in the user-configured layout of said medical information display image in response to user selection of an image element, said image element being associated with said trigger data item and displayed in said medical information display image in the user-configured layout;
displaying a preview image of said populated data item fields in the user-configured layout in a visual format substantially the same as the visual format said populated data items fields are to have in said medical information display image; and
enabling a modification of at least one of the selected data items and selected trigger data item using the generated display image and without exiting preview image.

22. A method for processing medical information concerning administration of treatment to a patient, comprising the steps of generating, by a processor:
generating a display image enabling a user to configure a layout of a medical information display image including user selection of,
(a) a plurality of data items associated with an individual patient parameter for display in a preview display window in a user-configured visual format substantially the same as the visual format said data items are to have in a the medical information display image, the preview window enabling a user to selectively view a modification of said selected data items associated with the individual patient parameter without exiting the preview display window within the display image, and
(b) a particular data item of said plurality of data items as a trigger data item; and
searching by a command processor memory to retrieve an exemplary set of data values associated with the selected trigger data item to populate data item fields in said medical information display image in response to user selection of an image element associated with said trigger data item, said image element being displayed in said medical information display image.

* * * * *